(12) United States Patent
Mohr et al.

(10) Patent No.: US 10,781,367 B2
(45) Date of Patent: Sep. 22, 2020

(54) EFFECT PIGMENTS AND STRUCTURAL COLORANTS INCORPORATING FLUORESCENT PARTICLES

(71) Applicant: BASF CORPORATION, Florham Park, NJ (US)

(72) Inventors: Benjamin Mohr, Elmsford, NY (US); Urs Stadler, Madison, NJ (US)

(73) Assignee: BASF CORPORATION, Florham Park, NJ (US)

( * ) Notice: Subject to any disclaimer, the term of this patent is extended or adjusted under 35 U.S.C. 154(b) by 392 days.

(21) Appl. No.: 15/624,523

(22) Filed: Jun. 15, 2017

(65) Prior Publication Data

US 2017/0362503 A1    Dec. 21, 2017

Related U.S. Application Data

(60) Provisional application No. 62/352,824, filed on Jun. 21, 2016.

(51) Int. Cl.
| | | |
|---|---|---|
| *C09K 11/54* | (2006.01) | |
| *C09C 1/00* | (2006.01) | |
| *C09D 5/36* | (2006.01) | |
| *A61Q 1/02* | (2006.01) | |
| *A61Q 19/00* | (2006.01) | |

(Continued)

(52) U.S. Cl.
CPC ............ *C09K 11/54* (2013.01); *A61K 8/0258* (2013.01); *A61Q 1/02* (2013.01); *A61Q 19/00* (2013.01); *C09C 1/0024* (2013.01); *C09C 1/0039* (2013.01); *C09C 1/0051* (2013.01); *C09C 1/0066* (2013.01); *C09D 5/36* (2013.01); *A61K 2800/10* (2013.01); *A61K 2800/434* (2013.01); *A61K 2800/436* (2013.01); *A61K 2800/621* (2013.01); *A61K 2800/63* (2013.01); *A61K 2800/651* (2013.01); *C08K 3/22* (2013.01); *C09C 2200/102* (2013.01);

(Continued)

(58) Field of Classification Search
CPC ..... C09K 11/54; C09C 1/0015; C09C 1/0021; C09C 2200/102; C09C 2200/505; C09C 2200/50; C09C 2210/50; C09C 2210/10
See application file for complete search history.

(56) References Cited

U.S. PATENT DOCUMENTS 4,954,175 A * 9/1990 Ito .................... C09C 1/0078
106/417
6,565,770 B1 * 5/2003 Mayer ................ B82Y 10/00
106/403

(Continued)

FOREIGN PATENT DOCUMENTS

| JP | 2013-110209 | * | 6/2013 |
| WO | WO 2015/017722 | * | 2/2015 |
| WO | WO-2016/085874 A1 | | 6/2016 |

OTHER PUBLICATIONS

Translation of JP 2013-110209 {labeled Description (PatentsApplication2011-252701)}, Jun. 6, 2013.*

(Continued)

*Primary Examiner* — C Melissa Koslow
(74) *Attorney, Agent, or Firm* — Foley & Lardner LLP

(57) ABSTRACT

An effect pigment includes a substrate; an outer layer disposed above the substrate; and particles disposed above the substrate and at least partially entrapped by the outer layer, the particles comprising quantum dots.

14 Claims, 4 Drawing Sheets

(51) Int. Cl.
*A61K 8/02* (2006.01)
*C08K 3/22* (2006.01)

(52) U.S. Cl.
CPC .... *C09C 2200/505* (2013.01); *C09C 2210/50* (2013.01); *C09C 2220/10* (2013.01)

(56) References Cited

U.S. PATENT DOCUMENTS

| | | | |
|---|---|---|---|
| 6,875,264 | B2 | 4/2005 | Zimmermann et al. |
| 2008/0196847 | A1 | 8/2008 | Van Heiningen et al. |
| 2010/0322981 | A1 | 12/2010 | Bujard et al. |
| 2016/0145437 | A1* | 5/2016 | Ponce .................. C09C 1/0045 424/401 |
| 2016/0145438 | A1* | 5/2016 | Ponce .................. C09C 1/0015 424/401 |

OTHER PUBLICATIONS

Liu et al., "Controllable synthesis and change of emission color from green to orange of ZnO quantum dots using different solvents," New J. Chem., 2015, 39, 2881-2888 (Abstract Only).

Extended EP Search Report in EP Application No. 17176810.4, dated Dec. 19, 2017 (11 pages).

Li et al., "Significant Enhancements in the Fluorescence and Phosphorescence of ZnO Quantum Dots/SiO$_2$ Nanocomposites by Calcination," J. Phys. Chem. C, vol. 112, No. 44, 2008, pp. 17397-17401.

Li et al., "Transparent and Light-Emitting Epoxy Super-Nanocomposites Containing ZnO-QDs/SiO$_2$ Nanocomposite Particles as Encapsulating Materials for Solid-State Lighting," J. Phys. Chem. C, vol. 112, 2008, pp. 18616-18622.

Stein et al., "Morphological Control in Colloidal Crystal Templating of Inverse Opals, Hierarchical Structures, and Shaped Particles," Chem. Mater., vol. 20, 2008, pp. 649-666.

* cited by examiner

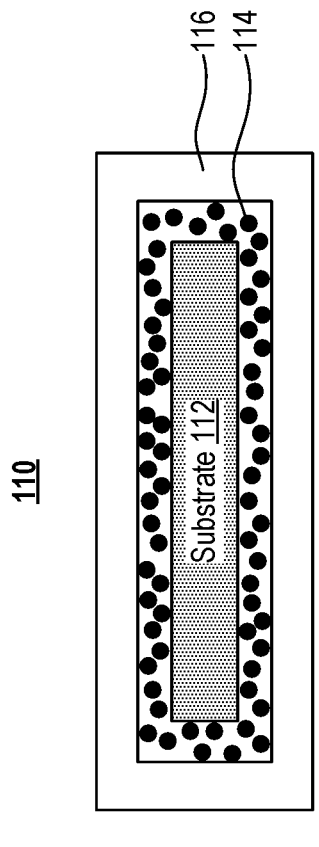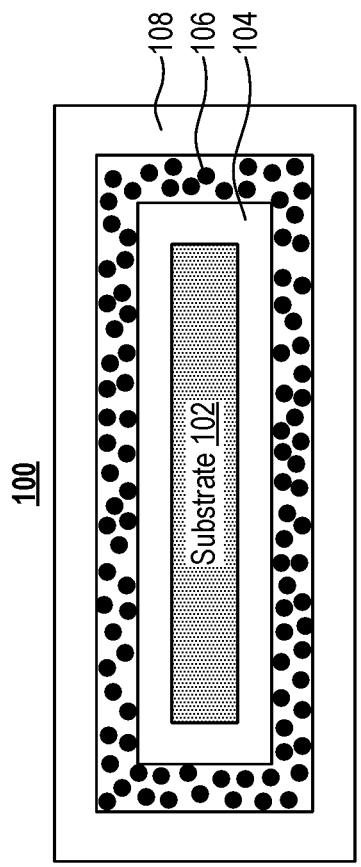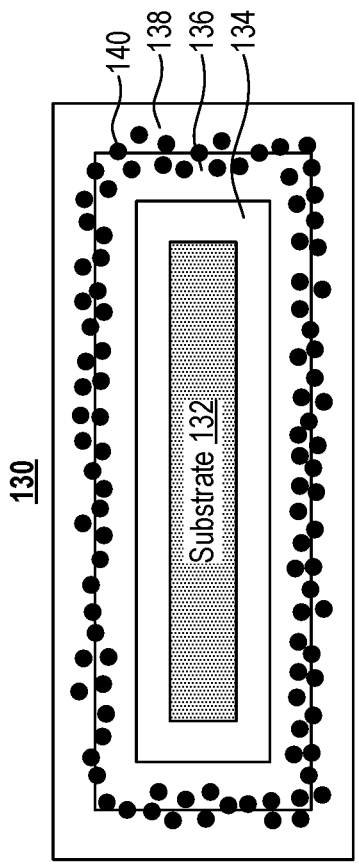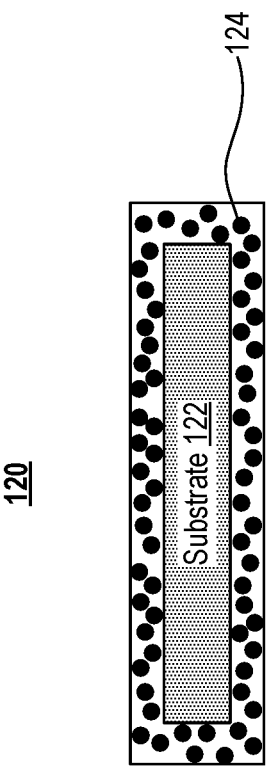

EFFECT PIGMENTS AND STRUCTURAL COLORANTS INCORPORATING FLUORESCENT PARTICLES

CROSS-REFERENCE TO RELATED APPLICATIONS

This application claims the benefit of priority to U.S. Application No. 62/352,824, filed on Jun. 21, 2016, the contents of which are incorporated herein by reference in their entirety.

FIELD OF THE INVENTION

This application is directed to effect pigments or structural colorants containing fluorescent particles, and methods of producing the same.

BACKGROUND

Effect pigments (sometimes also called gloss pigments, lustrous pigments, pearlescent pigments, interference pigments, or color variable pigments) are well known in the art. A widely used type of effect pigment includes mica platelets coated with metallic oxides, such as titanium dioxide. A thin titanium dioxide ($TiO_2$) coating produces a pearl-like or silvery luster, with the color produced by this thin layer of $TiO_2$ being a function of optical thickness of the $TiO_2$ layer. The term "combination pigment" refers to more complex pigments that may contain a coated platelet such as titanium dioxide coated mica to give a reflected color, and an absorption pigment or dye which absorbs some portion of the visible spectrum.

SUMMARY

The following summary provides a basic understanding of the embodiments of the disclosure. This summary is not an extensive overview of all contemplated aspects of the disclosure, and is not intended to identify all key or critical elements or to delineate the scope of any or all aspects of the disclosure. Its sole purpose is to present one or more aspects of the disclosure in a summary form as a prelude to the more detailed description of the invention that follows and the features described and particularly pointed out in the claims.

In one aspect of the present disclosure, an effect pigment comprises a substrate; an outer layer disposed above the substrate; and particles comprising one or more of quantum dots or structural colorant particles, wherein the particles are disposed above the substrate and are at least partially entrapped by the outer layer.

In another aspect of the present disclosure, a method of producing an effect pigment comprises depositing particles on a substrate followed by forming an outer layer over the particles, or co-depositing the particles and the outer layer on the substrate, wherein the outer layer at least partially entraps the particles.

BRIEF DESCRIPTION OF THE DRAWINGS

The above and other features of the present disclosure, their nature, and various advantages will become more apparent upon consideration of the following detailed description, taken in conjunction with the accompanying drawings, in which:

FIG. 1A illustrates a layer arrangement for an effect pigment, in accordance with an embodiment of the present disclosure.

FIG. 1B illustrates a layer arrangement for an effect pigment, in accordance with an embodiment of the present disclosure.

FIG. 1C illustrates a layer arrangement for an effect pigment, in accordance with an embodiment of the present disclosure.

FIG. 1D illustrates a layer arrangement for an effect pigment, in accordance with an embodiment of the present disclosure.

DETAILED DESCRIPTION

Figure 2:
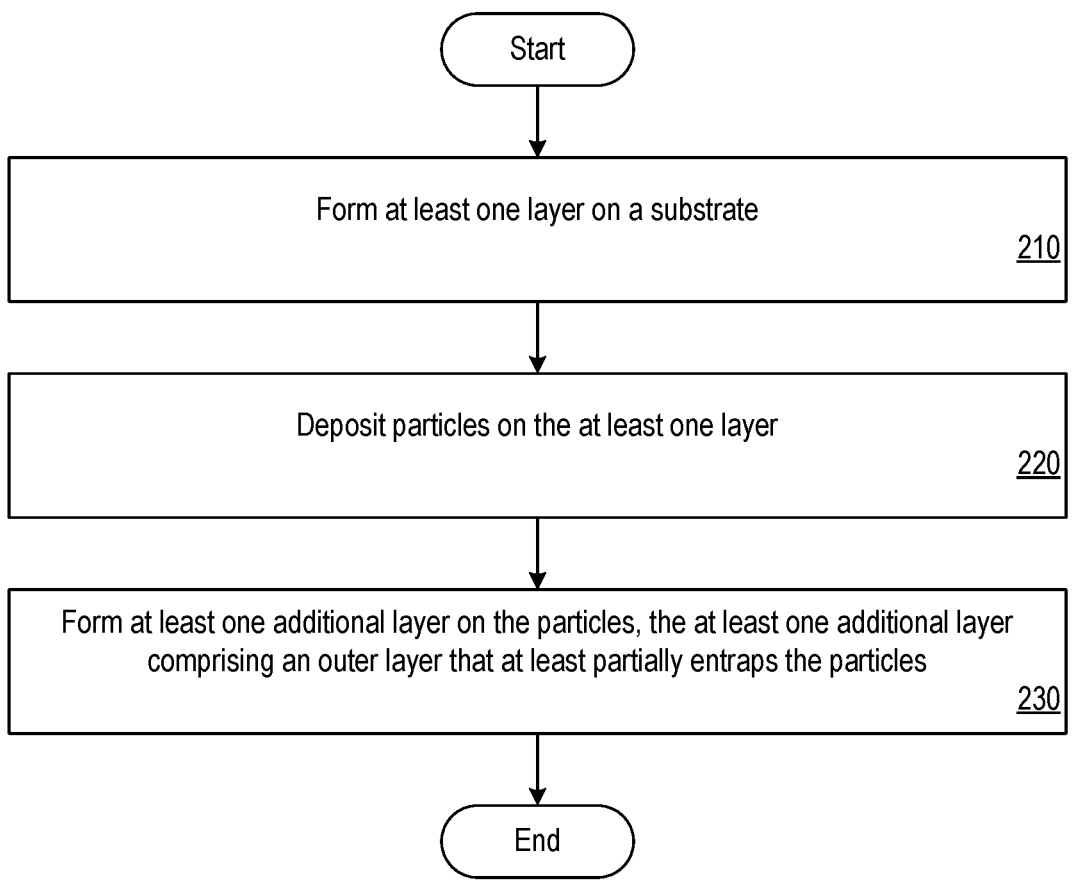
FIG. 2 is a block diagram illustrating a method for producing an effect pigment, in accordance with embodiments of the present disclosure.

The present disclosure is directed to combination effect pigments. In particular, the present disclosure is directed to combination effect pigments or structural colorants that incorporate fluorescent particles ("fluorescent effect pigments"). In certain embodiments, the fluorescent effect pigment includes quantum dots (e.g., zinc oxide quantum dots) covered by or encapsulated, or partially encapsulated, between a substrate and an outer layer. In some embodiments, the quantum dots can be absorbed onto a porous substrate before the deposition of a layer on the porous substrate. The quantum dots may be deposited, for example, by wet chemical deposition, chemical vapor deposition, or other processes. Particle deposition is followed by one or more overlayers. The one or more overlayers may be, for example, a high or low refractive index layer such as a metal oxide or $SiO_2$.

In certain embodiments, particles, such as zinc oxide quantum dots, were encapsulated into an effect pigment (e.g., having a glass flake substrate with a pearl interference color) in order to produce a fluorescent effect. The pigment may appear as a classic white/pearl/sparkly effect pigment under normal lighting conditions, while the effect pigment produces a yellow glow upon ultraviolet light exposure. Certain embodiments utilize zinc oxide quantum dots, which are nanoparticles that are under 5 nm in diameter. Due to quantum confinement, these particles are able to absorb UV light and produce a fluorescent emission color. The color of the fluorescent light can be tuned by adjusting the size of the particles. Zinc oxide particles may be tuned to produce blue, green, or yellow emission colors. In certain embodiments, the zinc oxide particles may have an average diameter from 0.1 nanometers to 200 nanometers, or from 0.1 nanometers to 15 nanometers in other embodiments. In certain embodiments, the quantum dots may have core-shell or rod-like morphologies. For example, those with rod-like morphologies may have a large aspect ratio (e.g., a length of 50 nanometers to 100 nanometers or greater, and a width of 0.5 nanometers to 10 nanometers).

Certain embodiments utilize structural colorants. Structural colorants are highly ordered structures from which color arises as a result of Bragg diffraction of natural light. Such materials may be or may be based on photonic materials including, but not limited to, opals, inverse opals, photonic shards, photonic spheres, composite photonic crystals. As used herein, the term "photonic material" refers to a material having at a degree of periodic variations in its structure, such as having periodic alternating high dielectric constant and low dielectric constant regions, that affect light propagation. A photonic material need not have perfect crystalline order, and may include defects throughout. For example, a photonic material may include structures that have short- and long-range periodic variations in its structure. In certain embodiments, a photonic material having a resonant frequency near a desired color range can be utilized. For example, such materials may be periodically structured with a periodicity matching the wavelength of a particular wavelength. In certain embodiments, such periodicity can exist in one dimension, two dimensions, or three dimensions. In certain embodiments, a photonic material is in a form of particles, such as an array of particles.

In certain embodiments, the photonic materials can be formed from materials such as oxides (e.g., silica, titania, zirconia, alumina, hafnia, beryllia, platinum oxide, molybdenum oxide, tungsten oxide, rhenium oxide, tantalum oxide, niobium oxide, chromium oxide, scandium, yttrium, lanthanum, ceria, rare earth oxides, inorganic sol-gel derived oxides, etc.), organic polymeric materials, inorganic polymeric materials (e.g., silicone), organic and inorganic mineral salts and crystals (e.g., carbonates, sulfates, phosphates, etc.), mixed salts, minerals (e.g., quartz, sapphire, etc.), metals, metal alloys, semiconductor materials (e.g., silicon), and combinations thereof. In certain embodiments, a photonic material may be incorporated into a pigment.

It is noted that the term "particle" as used herein may refer generally to both nanoparticles (particles having a maximum dimension of less than 1000 nanometers) or microparticles (particles having a minimum dimension of greater than 1000 nanometers and a maximum dimension of less than 1 millimeter), unless indicated otherwise. Moreover, a particle may also be formed from smaller particles, such as an opal particle that comprises a packed array of silica nanoparticles.

Low refractive index substances, such as $SiO_2$, may be part of a combination pigment to influence the optical performance. One example is the creation of a color variable pigment, as described in U.S. Pat. No. 6,875,264, which is hereby incorporated by reference herein in its entirety, and which discloses at least three layer effect pigments having, in sequence, a high refractive index layer, a low refractive index layer, and a high refractive index layer. A reflection color of the pigment may be a function of optical thickness of the layer or layers on the substrate.

The term "combination effect pigment" refers to a combination of two types of color producing phenomena within the same pigment. For example, the combination effect pigment produces color as a function of optical thickness of a layered coating (e.g., $TiO_2$ coatings on mica) on a substrate, that acts as a reflecting layer which is a function of optical thickness, and includes an absorbing colorant on the same substrate.

The term "optical layer" is well known in the art and refers to a coating or layer on a substrate where the coating or layer reflects color and the color is a function of the optical thickness of the coating, that is, the geometrical thickness times the refractive index of the coating. An optical thickness of about 80 nm to about 140 nm produce reflections which may be characterized as white, silvery, or pearly, and optical thicknesses of about 190 nm or more produce colored reflections. Typically, the thickness of the optical coating or layer will range from about 60 nm to about 800 nm. The optical layer is most typically a metal oxide layer.

The term "at least one layer", as used herein, refers to one or more layers. The layer may be organic or inorganic. The "at least one layer" may be of high refractive index, that is greater than or equal to 1.65 or of low refractive index, that is of less than 1.65. The "at least one layer" may be a metal oxide selected from $TiO_2$, $In_2O_3$, $ZrO_2$, $Fe_2O_3$, $Fe_3O_4$, $Cr_2O_3$, $CeO_2$, $ZnO$, $SnO_2$, and mixtures thereof. The metal oxides $TiO_2$, $Cr_2O_3$, $Fe_2O_3$ and $SnO_2$ are most typical. Furthermore, the "at least one layer" may be a metal oxide, $SiO_2$ a metal such brass, bronze, silver or aluminum. In some embodiments, magnetite may be incorporated into one or more layers, or may be present as a standalone layer.

There may be multiple layers on the substrate overlayering the particle deposition and these may be formed from the as above metal oxide, $SiO_2$, a metal such as brass, bronze, silver and aluminum.

As used herein, the term "substrate" refers to platy inorganic or organic treated or untreated materials. For example, such platy materials may include aluminum oxide, platy glass, perlite, aluminum, natural mica, synthetic mica, bismuth oxychloride, platy iron oxide, platy graphite, platy silica, bronze, stainless steel, natural pearl, boron nitride, copper flake, copper alloy flake, zinc flake, zinc alloy flake, zinc oxide, enamel, china clay, porcelain, titanium oxide, platy titanium dioxide, titanium suboxide, kaolin, zeolites, and combinations thereof.

As used herein, the term "platy" (e.g., when referring to a "platy substrate") is well understood in the art. The term "platy" may be used interchangeably with flake, flake-like, plate-like, platelet and flaky.

A platy substrate has two dimensions (length and width) of similar magnitude and characteristically much greater than the third dimension (i.e., the thickness of the platy substrate). Platy substrates are useful for the application of the metal oxide coating and/or $SiO_2$ and deposition or co-deposition of the particles.

In some embodiments, a diameter of a platy substrate (e.g., assuming a disc-like shape) may range from about 0.1 to about 350 microns, from about 5 to about 250 micrometers, or from about 1 to about 150 micrometers. In some embodiments, the diameter ranges from about 5 to about 50 or about 100 micrometers.

In some embodiments, the substrate may be selected from a group consisting of iron oxide, synthetic mica, natural mica, basic lead carbonate, flaky barium sulfate, $SiO_2$, $Al_2O_3$, $TiO_2$, glass flakes, $ZnO$, $ZrO_2$, $SnO_2$, $BiOCl$, chromium oxide, BN, MgO flakes, $Si_3N_4$, graphite, aluminum, titanium, aluminum alloys, bronzes, iron, and perlite. In some embodiments, a platy substrate may be selected from a group consisting of synthetic mica, natural mica, $SiO_2$ flakes, $Al_2O_3$ flakes, $TiO_2$ flakes, $Fe_2O_3$ flakes, $BiOCl$, and glass flakes.

In some embodiments, the substrate may be treated or untreated. For example, the substrate may be treated with one or more agents, such as silicones and coupling agents. In other embodiments, the substrate may be mechanically treated to smooth the surface, or plasma or radiation treated to activate the surface before deposition of particles and/or one or more layers.

In some embodiments, the substrate may also be a mixture of identical or different substrates, each having different particle sizes. The substrate mixture can include two, three or more different substrates, for example. In one embodiment, a mixture may include two or more of natural mica, synthetic mica, or glass flakes.

When applying the particles to the substrate directly or onto a $SiO_2$ layer, a porous substrate, for example, may be advantageous in some embodiments. A porous substrate or silica coated substrate can be treated with particles via incipient wetness impregnation. Incipient wetness is a process in which a solid support is impregnated with the maximum amount of solution that it can absorb without having any excess solution. After impregnation, the material is dried. In some embodiments, the solution includes a particle dispersion.

In some embodiments, particles are deposited as a stand-alone (single) layer disposed between the substrate and another layer (e.g., a layer comprising a different material than particles), and/or disposed between two layers (e.g., two layers comprising different material than particles). In some embodiments, particles are co-deposited with a layer, such that the particles are dispersed within the layer (e.g., a $TiO_2$ layer that includes particles dispersed throughout). In some embodiments, particles may be disposed between the substrate and another layer and/or between other pairs of adjacent layers. In some embodiments, particles may be deposited as a standalone (single layer) and may be partially dispersed within at least one of its adjacent layers. In some embodiments, various combinations of particles may be present as one or more particles layers along with one or more non-particle layers having particles dispersed therein.

FIGS. 1A-1D illustrate different layer arrangements for an effect pigment in accordance with various embodiments of the present disclosure. The illustrations use generic terminology (e.g., layer, substrate, etc.) to denote the morphology, and it is to be understood that such generic terminology may correspond to any of the materials disclosed herein (e.g., a substrate may correspond to a platy substrate, an outer layer may comprises $TiO_2$, particles may correspond to zinc oxide quantum dots, structural colorant particles, etc.). Moreover, it is noted that the drawings are not necessarily to scale. Other layer arrangements are also possible, and are described throughout the disclosure.

Pigment 100 includes a substrate 102 (e.g., a platy substrate), an intermediate layer 104 (e.g., a metal oxide layer), an outer layer 108 (e.g., a metal oxide layer), and a particle layer 106 disposed between the intermediate layer 104 and the outer layer 108. In some embodiments, the particle layer 106 comprises a zinc oxide quantum dots. In some embodiments, the particle layer is a layer (e.g., a metal oxide layer) having particle dispersed therein.

Pigment 110 includes a substrate 112 (e.g., a platy substrate), an outer layer 116 (e.g., a metal oxide layer), and a particle layer 114 disposed between the substrate 112 and the outer layer 116.

Pigment 120 includes a substrate 122 (e.g., a platy substrate) and an outer layer 124 (e.g., a metal oxide layer) having particles entrapped therein.

Pigment 130 includes a substrate 132 (e.g., a platy substrate), an inner layer 134 (e.g., a metal oxide layer), an intermediate layer 136 (e.g., a metal oxide layer), and an outer layer 138 (e.g., a metal oxide layer). Particles 140 may be dispersed at least partially throughout each of the intermediate layer 136 and the outer layer 140.

In some embodiments, the particles may be coated with hydrophilic ligands that help the particles to remain dispersed in an aqueous medium.

Various loadings of particles may be utilized. As used herein, "wt. %" refers to an amount of loading of a material versus a starting substrate onto which the material is loaded. For example, 5 wt. % of particles would correspond to 5 g of particles loaded onto 100 g of substrate.

In some embodiments, particles (e.g., quantum dots or structural colorant particles) may be present in the effect pigment in an amount, for example, up to 50.00 wt. %, up to 40.00 wt. %, up to 30.00 wt. %, from about 0.01 wt. % to about 50.00 wt. %, from about 0.01 wt. % to about 40.00 wt. %, from about 0.01 wt. % to about 30.00 wt. %, about 0.01 wt. % to about 25.00 wt. %, about 0.01 wt. % to about 20.00 wt. %, about 0.01 wt. % to about 15.00 wt. %, about 0.01 wt. % to about 10.00 wt. %, about 0.01 wt. % to about 5.00 wt. %, about 0.01 wt. % to about 3.00 wt. %, about 0.01 wt. % to about 1.00 wt. %, about 0.01 wt. % to about 0.80 wt. %, about 0.01 wt. % to about 0.50 wt. %, about 0.01 wt. % to about 0.30 wt. %, or about 0.01 wt. % to about 0.10 wt. %, based on a total weight of the uncoated substrate.

In some embodiments, particles may be present in the effect pigment in an amount from, for example, about 0.10 wt. % to about 50.00 wt. %, about 0.10 wt. % to about 40.00 wt. %, about 0.10 wt. % to about 30.00 wt. %, about 0.10 wt. % to about 25.00 wt. %, about 0.10 wt. % to about 20.00 wt. %, about 0.10 wt. % to about 15.00 wt. %, about 0.10 wt. % to about 10.00 wt. %, about 0.10 wt. % to about 5.00 wt. %, about 0.10 wt. % to about 3.00 wt. %, about 0.10 wt. % to about 1.00 wt. %, about 0.10 wt. % to about 0.80 wt. %, about 0.10 wt. % to about 0.50 wt. %, or about 0.10 wt. % to about 0.30 wt. %, based on a total weight of the uncoated substrate.

In some embodiments, particles may be present in the effect pigment in an amount from, for example, about 1.00 wt. % to about 50.00 wt. %, about 1.00 wt. % to about 40.00 wt. %, about 1.00 wt. % to about 30.00 wt. %, about 1.00 wt. % to about 25.00 wt. %, about 1.00 wt. % to about 20.00 wt. %, about 1.00 wt. % to about 15.00 wt. %, about 1.00 wt. % to about 10.00 wt. %, about 1.00 wt. % to about 5.00 wt. %, or about 1.00 wt. % to about 3.00 wt. %, based on a total weight of the uncoated substrate.

In some embodiments, particles may be present in the effect pigment in an amount from, for example, about 10.00 wt. % to about 50.00 wt. %, about 10.00 wt. % to about 40.00 wt. %, about 10.00 wt. % to about 30.00 wt. %, about 10.00 wt. % to about 25.00 wt. %, about 10.00 wt. % to about 20.00 wt. %, or about 10.00 wt. % to about 15.00 wt. %, based on a total weight of the uncoated substrate.

In some embodiments, particles may be present in the effect pigment in an amount from, for example, about 10.00 wt. % to about 50.00 wt. %, about 10.00 wt. % to about 40.00 wt. %, about 10.00 wt. % to about 30.00 wt. %, about 10.00 to about 25.00 wt. %, about 10.00 to about 20.00 wt. %, or about 10.00 to about 15.00 wt. %, based on a total weight of the uncoated substrate.

In some embodiments, particles may be present in the effect pigment in an amount from, for example, about 15.00 wt. % to about 50.00 wt. %, about 15.00 wt. % to about 40.00 wt. %, about 15.00 wt. % to about 30.00 wt. %, about 15.00 to about 25.00 wt. %, or about 15.00 to about 20.00 wt. %, based on a total weight of the uncoated substrate.

In some embodiments, particles may be present in the effect pigment in an amount, for example, from 0.01 wt. % to 50.00 wt. %, from 0.01 wt. % to 40.00 wt. %, from 0.01 wt. % to 30.00 wt. %, 0.01 wt. % to 25.00 wt. %, 0.01 wt. % to 20.00 wt. %, 0.01 wt. % to 15.00 wt. %, 0.01 wt. % to 10.00 wt. %, 0.01 wt. % to 5.00 wt. %, 0.01 wt. % to 3.00 wt. %, 0.01 wt. % to 1.00 wt. %, 0.01 wt. % to 0.80 wt. %, 0.01 wt. % to 0.50 wt. %, 0.01 wt. % to 0.30 wt. %, or 0.01 wt. % to 0.10 wt. %, based on a total weight of the uncoated substrate.

In some embodiments, particles may be present in the effect pigment in an amount from, for example, 0.10 wt. % to 50.00 wt. %, 0.10 wt. % to 40.00 wt. %, 0.10 wt. % to 30.00 wt. %, 0.10 wt. % to 25.00 wt. %, 0.10 wt. % to 20.00 wt. %, 0.10 wt. % to 15.00 wt. %, 0.10 wt. % to 10.00 wt. %, 0.10 wt. % to 5.00 wt. %, 0.10 wt. % to 3.00 wt. %, 0.10 wt. % to 1.00 wt. %, 0.10 wt. % to 0.80 wt. %, 0.10 wt. % to 0.50 wt. %, or 0.10 wt. % to 0.30 wt. %, based on a total weight of the uncoated substrate.

In some embodiments, particles may be present in the effect pigment in an amount from, for example, 1.00 wt. % to 50.00 wt. %, 1.00 wt. % to 40.00 wt. %, 1.00 wt. % to 30.00 wt. %, 1.00 wt. % to 25.00 wt. %, 1.00 wt. % to 20.00 wt. %, 1.00 wt. % to 15.00 wt. %, 1.00 wt. % to 10.00 wt. %, 1.00 wt. % to 5.00 wt. %, or 1.00 wt. % to 3.00 wt. %, based on a total weight of the uncoated substrate.

In some embodiments, particles may be present in the effect pigment in an amount from, for example, 10.00 wt. % to 50.00 wt. %, 10.00 wt. % to 40.00 wt. %, 10.00 wt. % to 30.00 wt. %, 10.00 wt. % to 25.00 wt. %, 10.00 wt. % to 20.00 wt. %, or 10.00 wt. % to 15.00 wt. %, based on a total weight of the uncoated substrate.

In some embodiments, particles may be present in the effect pigment in an amount from, for example, 15.00 wt. % to 50.00 wt. %, 15.00 wt. % to 40.00 wt. %, 15.00 wt. % to 30.00 wt. %, 15.00 to 25.00 wt. %, or 15.00 to 20.00 wt. %, based on a total weight of the uncoated substrate.

In some embodiments, the particles are deposited either directly onto the substrate or onto one of the layers on the substrate. The particles may be interposed as a particle layer between the substrate and the "at least one layer". The covering layer substantially covers the particle layer. The covering layer may be a metal oxide, $SiO_2$, or a metal such as brass, bronze, silver, or aluminum.

Method of Preparing an Effect Pigment

FIG. 2 is a block diagram illustrating a method 200 for producing an effect pigment, such as a fluorescent effect pigment, in accordance with embodiments of the present disclosure.

At block 210, at least one layer is formed on a substrate. In some embodiments, the substrate is a platy substrate, as described herein. The at least one layer may include a single layer or multiple layers, with each being independently selected from, for example, a metal oxide, $SiO_2$, or a non-oxide metal (e.g., aluminum, silver, brass or bronze). In some embodiments, block 210 may be modified such that no layers are deposited onto the substrate, such that particle may be later deposited onto the substrate directly with no intervening layers in between.

In some embodiments, substrate may be in a suspension or slurry, and can be treated in order to deposit the at least one layer. Further the at least one layer may be present in various crystalline forms (e.g., a $TiO_2$ layer may be anatase or rutile). In some embodiments, the at least one layer may be deposited via chemical vapor deposition.

At block 220, particles are deposited on the at least one layer. In some embodiments, the particles are deposited via wet chemical deposition. In some embodiments, the particles are deposited via chemical vapor deposition. In other embodiments, other techniques may be utilized for depositing the particles, such as depositing particle seeds and controlling the growth in situ. In some embodiments, wet chemical deposition may be performed by forming a slurry or suspension of particles and the substrate, with the slurry having a particular pH.

At block 230, at least one additional layer is formed on the particles, the at least one additional layers comprising an outer layer that at least partially entraps the particles. In some embodiments, the particles may be at least partially dispersed in the one or more additional layers. The effect pigment may then be dried after the outer layer is formed. The one or more additional layers may at least partially entrap (or completely entrap) the particles, which minimizes bleeding through of free particles.

Figure 3:
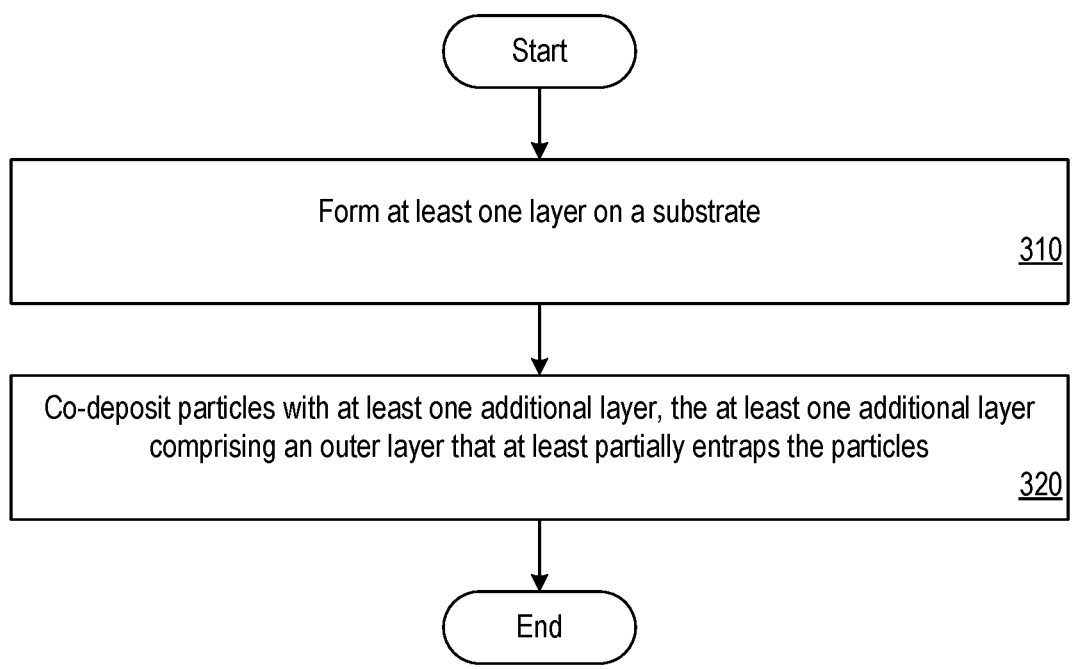
FIG. 3 is a block diagram illustrating a method for producing an effect pigment, in accordance with embodiments of the present disclosure.

FIG. 3 is a block diagram illustrating another method 300 for producing an effect pigment in accordance with embodiments of the present disclosure.

At block 310, at least one layer is formed on a substrate. In some embodiments, the substrate is a platy substrate, as described herein. Block 210 may be performed in a substantially similar manner as block 210 of FIG. 2. At block 320, particles are deposited on the at least one additional layer. For example, the particles, when co-deposited with another layer, may be dispersed as particles throughout the layer.

In each of methods 200 and 300, additional particles depositions and layer depositions may be performed as desired.

Figure 4:
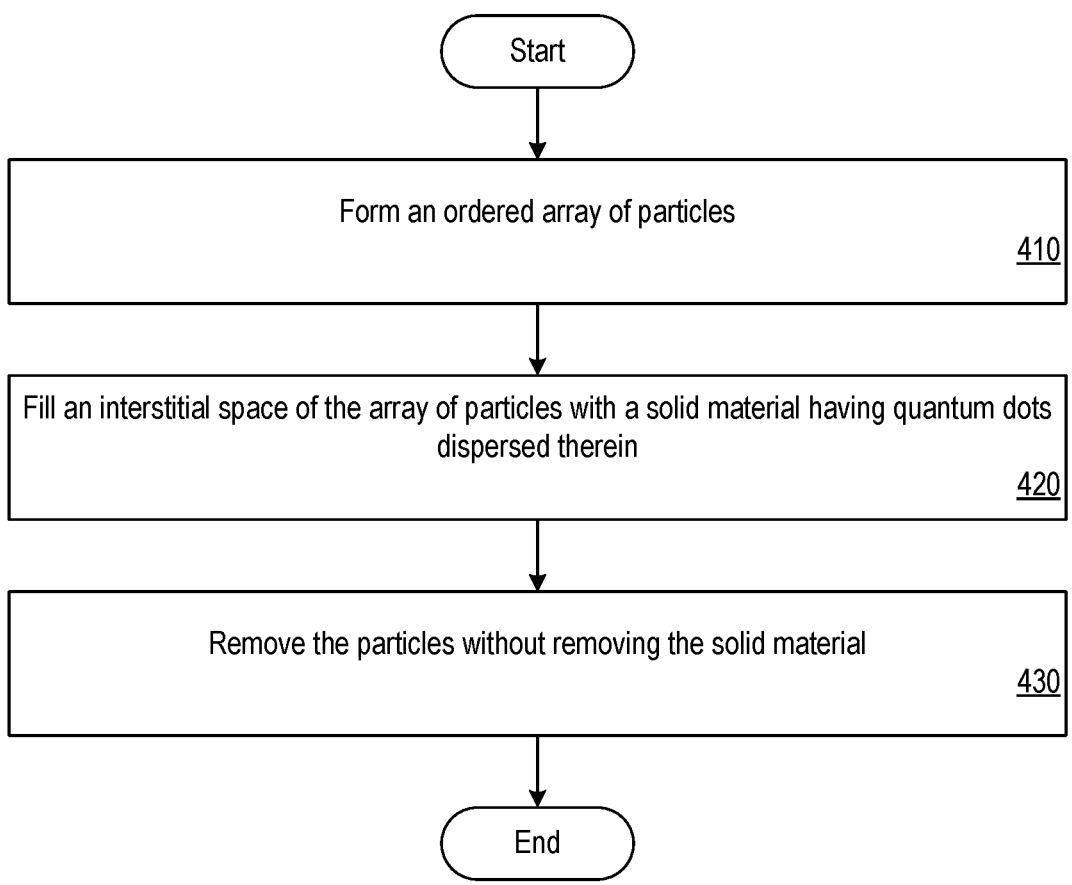
FIG. 4 is a block diagram illustrating a method for producing an inverse opal structure, in accordance with embodiments of the present disclosure.

FIG. 4 is a block diagram illustrating another method 400 for producing an inverse opal structure in accordance with embodiments of the present disclosure.

At block 410, an ordered array of particles is formed. In one embodiment, the particles comprise spherical particles or any other suitable shape. In one embodiment, the particles comprise silica, polymethylmethacrylate, other suitable materials, and combinations thereof.

At block 420, the interstitial space of the array of particles with a solid material having quantum dots dispersed therein. In one embodiment, the interstitial space is filled by depositing the solid material via wet chemical deposition, chemical vapor deposition, or any other suitable deposition method. In one embodiment, the solid material comprises titanium oxide and/or other suitable materials. In one embodiment, the quantum dots have an average diameter from 0.1 nanometers to 200 nanometers, from 0.1 nanometers to 100 nanometers, from 0.1 nanometers to 10 nanometers, or from 0.1 nanometers to 1 nanometer. In one embodiment, the quantum dots comprise zinc oxide quantum dots.

At block 430, the particles are removed without removing the solid material such that the remaining solid material defines the inverse opal structure. The remaining solid material contains quantum dots dispersed throughout. In one embodiment, the particles are removed by calcining the particles and the solid material.

EXAMPLES

The following examples are set forth to assist in understanding the embodiments described herein and should not be construed as specifically limiting the embodiments described and claimed herein. Such variations, including the substitution of all equivalents now known or later developed, which would be within the purview of those skilled in the art, and changes in formulation or minor changes in experimental design, are to be considered to fall within the scope of the embodiments incorporated herein.

Example 1. Synthesis of Zinc Oxide Quantum Dots

Zinc oxide particles were produced according to the following process. Initially, 9.8 g of zinc acetate was dissolved in 300 g of ethanol. The solution was placed under nitrogen atmosphere with the temperature raised to 70° C.

Once the zinc fully dissolved, a solution of potassium hydroxide in ethanol (4.8 g potassium hydroxide in 100 g of ethanol) was rapidly added. After the temperature recovered, the solution was allowed to react for 20 minutes. The reaction was monitored using UV-light. Once the optimal fluorescence was been obtained, the sample was removed from heat. The zinc oxide quantum dots suspended in ethanol were then used to synthesize effect pigments.

Example 2. Synthesis of a Pigment Having a Substrate/$TiO_2$/ZnO/$SiO_2$ Structure A 10% aqueous slurry containing 230 g of glass flakes was heated to 80° C. and stirred. The pH was adjusted to 1.3 with 28% w/w aq. HCl, then 43 g of a 20% w/w aq. $SnCl_4$ solution was pumped in at a pH of 1.3 at 2 mL/min. A 25% w/w aq. $TiOCl_2$ solution was subsequently added at 2.4 g/min. Once a given amount of $TOCl_2$ had been added, the sample was filtered, washed and calcined. 50 g of the calcined glass flakes was then suspended in water and heated to 70° C. Approximately 1 wt. % zinc oxide nanoparticles were added at 70° C. with a pH of 7.8 and at a flow rate of 2 mL/min. Once the zinc oxide had been added, the solution was stirred for an additional 30 minutes. 20 g of $Na_2SiO_3$ was then precipitated onto the substrate to create an outer layer. The $Na_2SiO_3$ was added at a rate of 2 g/min and HCl was used to maintain the pH at 7.8. Following the reaction described, the slurry was filtered, washed, and dried at 65° C. overnight.

The zinc oxide treated $TiO_2$ coated glass flakes were compared to untreated titania-coated glass flakes as a drawdown comprised of 6% pigment in lacquer. The bulk color of the zinc oxide-treated flakes was visually very similar to untreated flakes under normal lighting conditions. Under UV-light, the zinc oxide-treated flakes demonstrated fluorescence.

Example 3. Synthesis of Pigment Having Substrate/$TiO_2$/ZnO+$SiO_2$ Structure

A 10% aqueous slurry containing 230 g of glass flakes was heated to 80° C. and stirred. The pH was adjusted to 1.3 with 28% w/w aq. HCl, then 43 g of a 20% w/w aq. $SnCl_4$ solution was pumped in at a pH of 1.3 at 2 mL/min. A 25% w/w aq. $TiOCl_2$ solution was subsequently added at 2.4 g/min. Once a given amount of $TOCl_2$ had been added, the sample was filtered, washed, and calcined. 50 g of the calcined glass flakes was then suspended in water and heated to 70° C. The equivalent of 1 wt. % zinc oxide nanoparticles were added at 70° C. with a pH of 7.8 at a flow rate of 2 mL/min. At the same time, 20 g of $Na_2SiO_3$ were co-deposited with the zinc oxide onto the substrate. The $Na_2SiO_3$ was added at a rate of 2 g/min and HCl was used to maintain the pH at 7.8. Following the reaction described, the slurry was filtered, washed, and dried at 65° C. overnight.

The zinc oxide treated $TiO_2$-coated glass flakes were compared to untreated titania-coated glass flakes as a drawdown comprised of 6% pigment in lacquer. The bulk color of the zinc oxide-treated flakes was visually very similar to untreated flakes under normal lighting conditions. Under UV-light, the zinc oxide treated flakes demonstrated fluorescence.

Example 4. Synthesis of Pigment Having Substrate/$TiO_2$/ZnO+$SiO_2$ Structure

A 10% aqueous slurry containing 230 g of glass flakes was heated to 80° C. and stirred. The pH was adjusted to 1.3 with 28% w/w aq. HCl, then 43 g of a 20% w/w aq. $SnCl_4$ solution was pumped in at a pH of 1.3 at 2 mL/min. A 25% w/w aq. $TiOCl_2$ solution was subsequently added at 2.4 g/min. Once a given amount of $TiCl_4$ had been added, the sample was filtered, washed, and calcined. 50 g of the calcined glass flakes were suspended in 1L of isopropanol, 20 mL of ammonium hydroxide, and 200 mL of water. The slurry was heated to 60° C. Approximately 1 wt. % zinc oxide nanoparticles were added to the slurry a flow rate of 2 mL/min. 20 g of 98% TEOS in neat form was dumped into the slurry. The slurry was mixed for 12 hours at this temperature in order to complete the formation of a silica film. Following the reaction described, the slurry was filtered, washed, and dried at 65° C. overnight.

The zinc oxide-treated $TiO_2$ coated glass flakes were compared to untreated titania-coated glass flakes as a drawdown comprised of 6% pigment in lacquer. The bulk color of the zinc oxide-treated flakes was visually very similar to untreated flakes under normal lighting conditions. Under UV-light, the zinc oxide treated flakes demonstrated fluorescence.

Example 5. Preparation of Inverse Opal Structure

Spherical polystyrene particles were self-assembled into a close-packed array by controlled evaporation of water. Silica and zinc oxide quantum dots were subsequently or simultaneously filled into the interstitial space between the polystyrene particles. Upon calcination a silica inverse opal structure containing the zinc oxide quantum dots forms. Calcination also results in the removal of polystyrene particles. A silica inverse opal structure (structural color) containing fluorescent zinc oxide quantum dots is the product.

Illustrative Applications of Embodiments

The pigments according to the present disclosure can be used for all customary purposes, for example, for coloring polymers in a bulk material, coatings (including effect finishes and those for the automotive sector), printing inks (including offset printing, intaglio printing, gravure, bronzing, and flexographic printing), applications in cosmetics, ink-jet-printing, dyeing textiles, laser marking of papers and plastics, and lighting technologies (e.g., electronic displays). Such applications are known from reference works such as, for example, "Industrielle Organische Pigmente" (W. Herbst and K. Hunger, VCH Verlagsgesellschaft mbH, Weinheim—New York, $2^{nd}$, completely revised edition, 1995).

A paint, coating, printing ink, plastic, cosmetic formulation, laser marking, pigment composition or dry preparation, and a cosmetic formulation are example embodiments in which a effect pigment of the present disclosure may be incorporated.

In one embodiment, the effect pigment is part of a cosmetic composition. The form of the cosmetic composition can be any form normally used for cosmetics such as a cream, emulsion, foam, gel, lotion, milk, mousse, ointment, paste, powder, spray, or suspension. The cosmetic composition can be any colored cosmetic used on the skin, hair, eyes, or lips, such as concealing sticks, foundation, stage make-up, mascara (cake or cream), eye shadow (liquid, pomade, powder, stick, pressed, or cream), hair color, lipsticks, lip gloss, kohl pencils, eye liners, blushers, eyebrow pencils, and cream powders. Other exemplary cosmetic compositions include, but are not limited to, nail enamel, skin glosser stick, hair sprays, face powder, leg-makeup, insect repellent lotion, nail enamel remover, nail enamel base, perfume lotion, and shampoos of all types (gel or liquid). In addition, the claimed compositions can be used in shaving cream (concentrate for aerosol, brushless, lathering), hair groom, cologne stick, cologne, cologne emollient, bubble bath, body lotion (moisturizing, cleansing, analgesic, astringent), after shave lotion, after bath milk and sunscreen lotion. For a review of cosmetic applications, see Cosmetics: Science and Technology, 2nd Ed., Eds: M. S. Balsam and Edward Sagarin, Wiley-Interscience (1972) and deNavarre; and The Chemistry and Science of Cosmetics, 2nd Ed., Vols 1 and 2 (1962), Van Nostrand Co. Inc., Vols 3 and 4 (1975), Continental Press; both of which are hereby incorporated by reference herein in their entireties.

The cosmetic composition may comprise at least one cosmetically acceptable auxiliary agent. Cosmetically acceptable auxiliary agents include, but are not limited to, carriers, excipients, emulsifiers, surfactants, preservatives, fragrances, perfume oils, thickeners, polymers, gel formers, dyes, absorption pigments, photo protective agents, consistency regulators, antioxidants, antifoams, antistats, resins, solvents, solubility promoters, neutralizing agents, stabilizers, sterilizing agents, propellants, drying agents, opacifiers, cosmetically active ingredients, hair polymers, hair and skin conditioners, graft polymers, water-soluble or dispersible silicone-containing polymers, bleaches, care agents, colorants, tinting agents, tanning agents, humectants, refatting agents, collagen, protein hydrolyzates, lipids, emollients and softeners, tinting agents, tanning agents, bleaches, keratin-hardening substances, antimicrobial active ingredients, photofilter active ingredients, repellant active ingredients, hyperemic substances, keratolytic and keratoplastic substances, antidandruff active ingredients, antiphlogistics, keratinizing substances, active ingredients which act as antioxidants and/or as free-radical scavengers, skin moisturizing or humectants substances, refatting active ingredients, deodorizing active ingredients, sebostatic active ingredients, plant extracts, antierythematous or antiallergic active ingredients, and mixtures thereof. Cosmetic formulations are known in the art. See, for instance, U.S. Patent Application Publication Nos. 2008/0196847 and 2010/0322981.

The effect pigment may be added in any tinctorially effective amount to the paint, coating, printing ink, high molecular weight organic material, cosmetic formulation, laser marking, pigment composition, or dry preparation.

The effect pigment may be added to such materials as paint, coating, printing ink, high molecular weight organic material, cosmetic formulation, laser marking, pigment composition, or dry preparation at concentrations ranging from 0.0001% wt/wt to 90% wt/wt, 0.001% wt/wt to 80% wt/wt, or 0.01% wt/wt to 50% wt/wt, based on a total weight of the material/formulation.

Illustrative Embodiments

The foregoing embodiments, as well as additional embodiments, are described below.

In one aspect of the present disclosure, an effect pigment comprises: a substrate; an outer layer disposed above the substrate; and particles disposed above the substrate and at least partially entrapped by the outer layer, the particles comprising quantum dots.

In any of the above embodiments, the particles comprise quantum dots. In certain embodiments, the quantum dots have an average diameter from 0.1 nanometer to 200 nanometers. In certain embodiments, the quantum dots comprise zinc oxide quantum dots.

In any of the above embodiments, the outer layer comprises a metal oxide selected from a group consisting of $SiO_2$, $TiO_2$, $In_2O_3$, $ZrO_2$, $Fe_2O_3$, $Fe_3O_4$, $Al_2O_3$, $Cr_2O_3$, $CeO_2$, $ZnO$, $SnO_2$, and combinations thereof. In certain embodiments, the particles are co-deposited with the outer layer. In certain embodiments, the particles are embedded within the outer layer. In certain embodiments, the outer layer comprises one or more of $SiO_2$ or $TiO_2$. In certain embodiments, the particles are deposited via wet chemical deposition.

In any of the above embodiments, the particles are present in the effect pigment from about 0.10 wt. % to about 50.00 wt. % based on a total weight of the substrate.

In any of the above embodiments, the substrate is a platy substrate. In certain embodiments, the platy substrate is selected from a group consisting of iron oxide, synthetic mica, natural mica, basic lead carbonate, flaky barium sulfate, $SiO_2$, $Al_2O_3$, $TiO_2$, glass, $ZnO$, $ZrO_2$, $SnO_2$, BiOCl, chromium oxide, BN, MgO flakes, $Si_3N_4$, graphite, aluminum, titanium, aluminum alloys, bronzes, iron, and perlite. In certain embodiments, the substrate comprises a glass flake.

In any of the above embodiments, the effect pigment further comprises an intermediate layer disposed between the outer layer and the substrate. In certain embodiments, the particles are disposed as a layer between the intermediate layer and the outer layer, or disposed as a layer between the substrate and the intermediate layer.

In any of the above embodiments, the effect pigment further comprises a plurality of layers disposed between the substrate and the outer layer. In certain embodiments, the particles are embedded within one or more of the plurality of layers. In certain embodiments, the particles are disposed as a layer between any adjacent pair of layers of the effect pigment.

In any of the above embodiments, the effect pigment further comprises a plurality of intermediate layers disposed between the substrate and the outer layer, wherein the substrate, the particles, the plurality of intermediate layers, and the outer layer collectively define a layer structure of the effect pigment selected from a group consisting of:
substrate/$SiO_2$/particles/$SiO_2$,
substrate/particles/$SiO_2$,
substrate/particles/$TiO_2$,
substrate/$TiO_2$/particles/$TiO_2$,
substrate/particles/$TiO_2$/$SiO_2$,
substrate/$TiO_2$/particles/$SiO_2$,
substrate/$SiO_2$/$TiO_2$/particles/$Fe_2O_3$,
substrate/$TiO_2$/particles/$SiO_2$/particles/$TiO_2$,
substrate/$Fe_2O_3$/$SiO_2$/particles/$TiO_2$/$SiO_2$,
substrate/$SnO_2$/$TiO_2$/particles/$TiO_2$,
substrate/$TiO_2$/$SiO_2$/particles/$Fe_2O_3$,
substrate/$TiO_2$/$SiO_2$/particles/$TiO_2$,
substrate/$TiO_2$/particles/$SiO_2$/$Fe_2O_3$,
substrate/$TiO_2$/particles/$SiO_2$/$TiO_2$,
substrate/$Fe_2O_3$/$SiO_2$/particles/$Fe_2O_3$,
substrate/$Fe_2O_3$/$SiO_2$/particles/$TiO_2$,
substrate/$Fe_2O_3$/particles/$SiO_2$/$Fe_2O_3$,
substrate/$Fe_2O_3$/particles/$SiO_2$/$TiO_2$,
substrate/$TiO_2$/$SiO_2$/particles/$Cr_2O_3$,
substrate/particles/$Fe_2O_3$,
substrate/$TiO_2$/$SiO_2$/$TiO_2$/particles/$TiO_2$,
substrate/$TiO_2$/$SiO_2$/particles/$TiO_2$,
substrate/particles/$SiO_2$/$TiO_2$,
substrate/$TiO_2$/$SiO_2$/$TiO_2$/particles/$SiO_2$, and substrate/$TiO_2$/$SiO_2$/particles/$SiO_2$. In certain embodiments, the particles are present as a single layer or dispersed within one or more adjacent layers of the layer structure.

In any of the above embodiments, the effect pigment is incorporated into a paint, ink-jet, coating, printing ink, plastic, cosmetic, glaze for ceramics, or glass.

In another aspect of the present disclosure, a method comprises: depositing particles onto a substrate followed by forming an outer layer over the particles; or co-depositing the particles and the outer layer onto the substrate, wherein the outer layer at least partially entraps the particles.

In any of the above embodiments, the method further comprises depositing an intermediate layer prior to depositing the particles. In certain embodiments, depositing or co-depositing the particles comprises depositing the particles via wet chemical deposition.

In another aspect of the present disclosure, a method for forming an inverse opal structure comprises: forming an ordered array of particles, the ordered array of particles defining an interstitial space; filling the interstitial space with a solid material having quantum dots dispersed therein; and removing the particles without removing the solid material, wherein the remaining solid material defines the inverse opal structure.

In any of the above embodiments, the solid material comprises titanium oxide.

In any of the above embodiments, the quantum dots have an average diameter from 0.1 nanometers to 200 nanometers. In certain embodiments, the quantum dots comprise zinc oxide quantum dots.

In any of the above embodiments, the particles comprise spherical particles. In certain embodiments, the spherical particles comprise silica or polymethylmethacrylate.

In any of the above embodiments, removing the particles comprises calcining the particles and the solid material.

In any of the above embodiments, filling the interstitial space comprises depositing the solid material via wet chemical deposition or chemical vapor deposition.

In another aspect of the present disclosure, an inverse opal structure comprises a framework defining a plurality of periodically spaced pores, wherein the framework comprises a solid material having quantum dots dispersed therein.

In any of the above embodiments, the solid material comprises titanium oxide.

In any of the above embodiments, the quantum dots have an average diameter from 0.1 nanometer to 200 nanometers. In certain embodiments, the quantum dots comprise zinc oxide quantum dots.

The use of the terms "a," "an," "the," and similar referents in the context of describing the materials and methods discussed herein (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the materials and methods and does not pose a limitation on the scope unless otherwise claimed. No language in the specification should be construed as indicating any non-claimed element as essential to the practice of the disclosed materials and methods.

Reference throughout this specification to "one embodiment," "certain embodiments," "one or more embodiments" or "an embodiment" means that a particular feature, structure, material, or characteristic described in connection with the embodiment is included in at least one embodiment of the present disclosure. Thus, the appearances of the phrases such as "in one or more embodiments," "in certain embodiments," "in one embodiment," or "in an embodiment" in various places throughout this specification are not necessarily referring to the same embodiment of the present disclosure. Furthermore, the particular features, structures, materials, or characteristics may be combined in any suitable manner in one or more embodiments.

Although the embodiments disclosed herein have been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents, and the above-described embodiments are presented for purposes of illustration and not of limitation.

What is claimed is:

1. An effect pigment comprising:
   a substrate;
   an outer layer disposed above the substrate;
   an intermediate layer disposed between the outer layer and the substrate, optionally wherein the intermediate layer comprises a plurality of layers disposed between the substrate and the outer layer; and
   particles disposed above the substrate;
   wherein:
   the particles comprise quantum dots; and
   the particles are:
   disposed as a layer between the intermediate layer and the outer layer,
   disposed as a layer between the substrate and the intermediate layer, or are embedded within the intermediate layer.

2. The effect pigment of claim 1, wherein the quantum dots have an average diameter from about 0.1 nanometer to about 200 nanometers.

3. The effect pigment of claim 1, wherein the quantum dots comprise zinc oxide quantum dots.

4. The effect pigment of claim 1, wherein the outer layer comprises a metal oxide selected from the group consisting of $SiO_2$, $TiO_2$, $In_2O_3$, $ZrO_2$, $Fe_2O_3$, $Fe_3O_4$, $Al_2O_3$, $Cr_2O_3$, $CeO_2$, ZnO, $SnO_2$, and a combination of any two or more thereof.

5. The effect pigment of claim 1, wherein the outer layer comprises one or more of $SiO_2$ or $TiO_2$.

6. The effect pigment of claim 1, wherein the particles are present in the effect pigment from about 0.10 wt. % to about 50 wt. % based on a total weight of the substrate.

7. The effect pigment of claim 1, wherein the substrate is a platy substrate selected from the group consisting of iron oxide, synthetic mica, natural mica, basic lead carbonate, flaky barium sulfate, $SiO_2$, $Al_2O_3$, $TiO_2$, glass, ZnO, $ZrO_2$, $SnO_2$, BiOCl, chromium oxide, BN, MgO flakes, $Si_3N_4$, graphite, aluminum, titanium, aluminum alloys, bronzes, iron, and perlite.

8. The effect pigment of claim 1, wherein the intermediate layer comprises the plurality of layers disposed between the substrate and the outer layer and the particles are embedded within one or more of the plurality of layers.

9. The effect pigment of claim 1, wherein the intermediate layer comprises the plurality of intermediate layers disposed between the substrate and the outer layer, wherein the substrate, the particles, the plurality of intermediate layers, and the outer layer collectively define a layer structure of the effect pigment selected from a group consisting of:

substrate/$SiO_2$/$TiO_2$/particles/$Fe_2O_3$,
substrate/$SnO_2$/$TiO_2$/particles/$TiO_2$,
substrate/$TiO_2$/$SiO_2$/particles/$Fe_2O_3$,
substrate/$TiO_2$/$SiO_2$/particles/$TiO_2$,
substrate/$Fe_2O_3$/$SiO_2$/particles/$Fe_2O_3$,
substrate/$Fe_2O_3$/$SiO_2$/particles/$TiO_2$,
substrate/$TiO_2$/$SiO_2$/particles/$Cr_2O_3$,
substrate/$TiO_2$/$SiO_2$/$TiO_2$/particles/$TiO_2$,
substrate/$TiO_2$/$SiO_2$/particles/$TiO_2$,
substrate/$TiO_2$/$SiO_2$/$TiO_2$/particles/$SiO_2$, and
substrate/$TiO_2$/$SiO_2$/particles/$SiO_2$.

10. A method of producing an effect pigment according to claim 1, the method comprising:

providing a substrate;
depositing an intermediate layer;
depositing particles;
and
depositing an outer layer;
wherein:
the particles are deposited before or after the intermediate layer,
or are embedded in the intermediate layer.

11. The method of claim 10, wherein depositing the particles comprises depositing the particles via wet chemical deposition.

12. An inverse opal structure comprising a framework defining a plurality of periodically spaced pores, wherein the framework comprises a solid material having quantum dots dispersed therein, and wherein the quantum dots comprise zinc oxide quantum dots.

13. The effect pigment of claim 1, wherein the particles are disposed as a layer between the intermediate layer and the outer layer.

14. The effect pigment of claim 1, wherein the particles are disposed as a layer between the substrate and the intermediate layer.

* * * * *